United States Patent
Enzmann et al.

(10) Patent No.: US 9,763,812 B2
(45) Date of Patent: Sep. 19, 2017

(54) DUAL ROTATIONAL STENT APPARATUS AND METHOD FOR ENDOVASCULAR TREATMENT OF ANEURYSMS

(71) Applicant: THE REGENTS OF THE UNIVERSITY OF CALIFORNIA, Oakland, CA (US)

(72) Inventors: Dieter Enzmann, Beverly Hills, CA (US); Issei Kan, Los Angeles, CA (US); Ichiro Yuki, Los Angeles, CA (US); Fernando Vinuela, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 117 days.

(21) Appl. No.: 14/622,148

(22) Filed: Feb. 13, 2015

(65) Prior Publication Data

US 2015/0216684 A1    Aug. 6, 2015

Related U.S. Application Data

(63) Continuation of application No. PCT/US2013/055484, filed on Aug. 17, 2013.

(Continued)

(51) Int. Cl.
*A61F 2/852* (2013.01)
*A61F 2/07* (2013.01)
(Continued)

(52) U.S. Cl.
CPC .............. *A61F 2/852* (2013.01); *A61F 2/07* (2013.01); *A61F 2/848* (2013.01);
(Continued)

(58) Field of Classification Search
CPC .... A61F 2/82; A61F 2/852; A61F 2/90; A61F 2/91
(Continued)

(56) References Cited

U.S. PATENT DOCUMENTS 5,749,880 A * 5/1998 Banas ................... A61F 2/07
                                                  606/198
6,010,529 A * 1/2000 Herweck .............. A61F 2/06
                                                  600/36

(Continued)

FOREIGN PATENT DOCUMENTS

EP    0822789 B1    3/1998
EP    2066269 B1    2/2012

OTHER PUBLICATIONS

Korean Intellectual Property Office (KIPO), International Search Report and Written Opinion, related PCT International Patent Application No. PCT/US2013/055484, issued Nov. 4, 2013, pp. 1-12, with claims searched, pp. 13-18.

*Primary Examiner* — Suzette J Gherbi
(74) *Attorney, Agent, or Firm* — O'Banion & Ritchey LLP; John P. O'Banion

(57) ABSTRACT

A coaxial stent system is described in which an inner treatment stent is configured to be coaxially positioned inside an outer anchoring stent. The outer anchoring stent is adapted for insertion into a blood vessel and anchoring to the blood vessel at a position where the outer anchoring stent spans a neck of an aneurysm. A method for endovascular treatment of aneurysms is also described.

18 Claims, 8 Drawing Sheets

Related U.S. Application Data

(60) Provisional application No. 61/684,388, filed on Aug. 17, 2012.

(51) Int. Cl.
  *A61F 2/848* (2013.01)
  *A61F 2/82* (2013.01)

(52) U.S. Cl.
  CPC ... *A61F 2002/823* (2013.01); *A61F 2002/826* (2013.01); *A61F 2220/0008* (2013.01); *A61F 2250/0023* (2013.01)

(58) Field of Classification Search
  USPC .................................................. 623/1.1–1.53
  See application file for complete search history.

(56) References Cited

U.S. PATENT DOCUMENTS

| | | | |
|---|---|---|---|
| 6,161,399 A * | 12/2000 | Jayaraman | D04B 1/14 623/1.5 |
| 6,520,984 B1 | 2/2003 | Garrison et al. | |
| 7,220,275 B2 * | 5/2007 | Davidson | A61F 2/82 623/1.35 |
| 7,550,003 B2 | 6/2009 | Sogard et al. | |
| 7,846,198 B2 * | 12/2010 | Hogendijk | A61F 2/88 606/194 |
| 9,186,267 B2 * | 11/2015 | Losordo | A61B 17/12118 |
| 2003/0225448 A1 * | 12/2003 | Gerberding | A61F 2/91 623/1.15 |
| 2004/0199243 A1 * | 10/2004 | Yodfat | A61F 2/01 623/1.16 |
| 2012/0130469 A1 | 5/2012 | Cragg et al. | |
| 2014/0303714 A1 * | 10/2014 | Edwin | A61F 2/07 623/1.13 |
| 2015/0025618 A1 * | 1/2015 | Kim | A61F 2/848 623/1.15 |
| 2015/0066134 A1 * | 3/2015 | Bonhoeffer | A61F 2/2418 623/1.16 |
| 2015/0148883 A1 * | 5/2015 | Hyodoh | A61F 2/90 623/1.2 |
| 2015/0190257 A1 * | 7/2015 | Cragg | A61F 2/07 623/1.12 |
| 2015/0196382 A1 * | 7/2015 | Richter | A61B 5/0215 623/1.15 |
| 2016/0151177 A1 * | 6/2016 | Connor | A61F 2/82 623/1.44 |

* cited by examiner

DUAL ROTATIONAL STENT APPARATUS AND METHOD FOR ENDOVASCULAR TREATMENT OF ANEURYSMS

CROSS-REFERENCE TO RELATED APPLICATIONS

This application is a 35 U.S.C. §111(a) continuation of PCT international application number PCT/US2013/055484 filed on Aug. 17, 2013 and incorporated herein by reference in its entirety, which claims priority to, and the benefit of, U.S. provisional patent application Ser. No. 61/684,388 filed on Aug. 17, 2012 and incorporated herein by reference in its entirety. Priority is claimed to each of the foregoing applications.

The above-referenced PCT international application was published as PCT International Publication No. WO 2014/028913 on Feb. 20, 2014, which publication is incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED IN A COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND

1. Technical Field

This technology pertains generally to endovascular treatment, and more particularly to a stent for endovascular treatment of cerebral aneurysms.

2. Background Discussion

Commercially available intracranial stents have been developed as an adjunctive technique for coil embolization of wide neck aneurysms. These stents are deployed across the neck of a cerebral aneurysm, they contain the coils, which are placed inside the lumen of the aneurysms, and they prevent the protrusion or escape of these coils. Since all these stents are designed with a low strut density to allow placement of coils through them, it is difficult to prevent blood flow from getting into aneurysms by using these stents alone.

Moreover, there is no commercially available stent with the ability to vary the blood flow through its walls for brain aneurysm therapy.

Most patients have distinct vascular configurations with respect to the parent artery to the aneurysm, and of the perforators near the target aneurysm.

Accordingly, an object of the technology described herein is a stent system and methods that allow for specific, tailored treatment of aneurysms according to patient need and anatomy.

Another object is minimally-invasive therapy of aneurysms in the form of blood flow reduction and redirection without the need for conventional filling materials and associated methods. At least some of these objectives will be met in the description provided below.

BRIEF SUMMARY

One aspect of the technology described herein is an endovascular treatment stent, referred to herein as a "dual-rotational stent," which is configured for endovascular treatment of cerebral aneurysms without the need for placing coils in the aneurysm lumen.

The endovascular treatment stent of the technology described herein comprises a compound stent device having an adjustable, variable strut density pattern. Thus, the stent can cover the orifice of the aneurysm causing blockage of blood flow (or marked reduction of blood flow) to occlude the aneurysm, while sparing blood flow to perforators or side branches near the aneurysm neck. Given the multiplicity of complex, asymmetrical designs, the stent enables minimally invasively therapy in the form of blood flow reduction and redirection without the need for conventional filling materials and methods.

Moreover, the endovascular treatment stent of the technology described herein has the ability to vary the blood flow through its walls for brain aneurysm therapy. The strut's density, which determines the porous nature of the stent wall, can be variably adjusted from low to high, with high virtually eliminating the passage of blood. In addition, a variable, 2-dimensional geometric pattern on the surface of the cylindrical stent wall provides additional flexibility in redirecting or obstructing blood flow.

Accordingly, a coaxial stent system is described in which an inner treatment stent is configured to be coaxially positioned inside an outer anchoring stent. In one embodiment, the outer anchoring stent is adapted for insertion into a blood vessel and anchoring to the blood vessel at a position where the outer anchoring stent spans a neck of an aneurysm. In one embodiment, the anchoring stent includes a plurality of flexible struts arranged in a low-density pattern to allow for radial blood flow between the struts, whereas the inner treatment stent includes a plurality of flexible struts configured in a pattern for controlling a volume of blood flow radially into the aneurysm. The inner treatment stent may have a variable density design, with a high density region configured to be positioned to minimize or occlude blood flow to the aneurysm, and a lower density region configured to be aligned adjacent one or more perforators or branch vessels to allow blood flow to the one or more perforators or branch vessels. A method for endovascular treatment of aneurysms is also described.

Further aspects of the technology described herein will be brought out in the following portions of the specification, wherein the detailed description is for the purpose of fully disclosing preferred embodiments of the technology described herein without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

Figure 1:
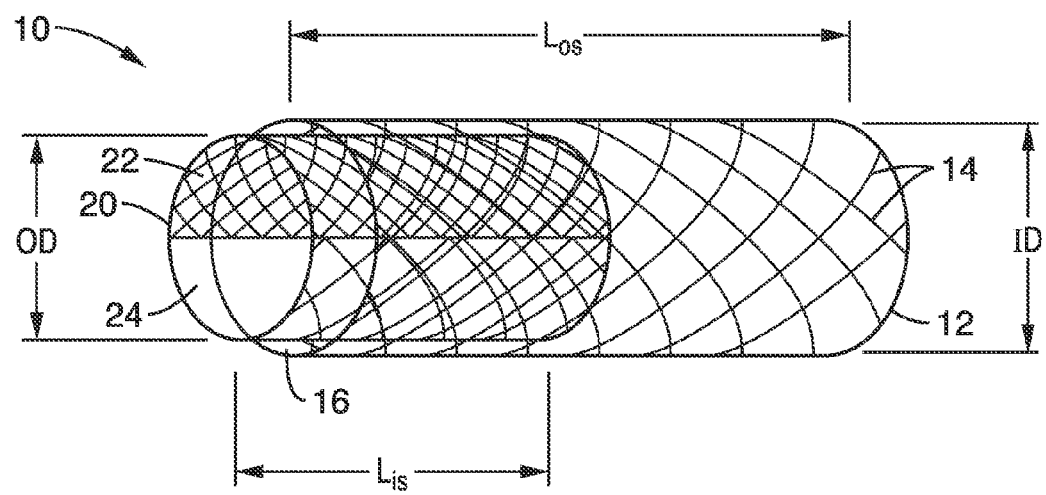
FIG. 1 is a schematic perspective view of the compound endovascular treatment stent assembly in accordance with the technology described herein.

FIG. 1 shows a perspective view of compound endovascular treatment stent assembly 10 in accordance with the technology described herein. Treatment stent assembly 10 comprises two primary but separate components: an outer anchoring stent 12 and inner treatment stent 20. The inner treatment stent 20 has an outside diameter OD sized to be at or slightly smaller than the inner diameter ID or inner wall 16 of the anchoring stent 12 such that the inner treatment stent 20 may be coaxially received in and be free to slideably engage or rotate with respect to the outer anchoring stent 12.

Figure 5:
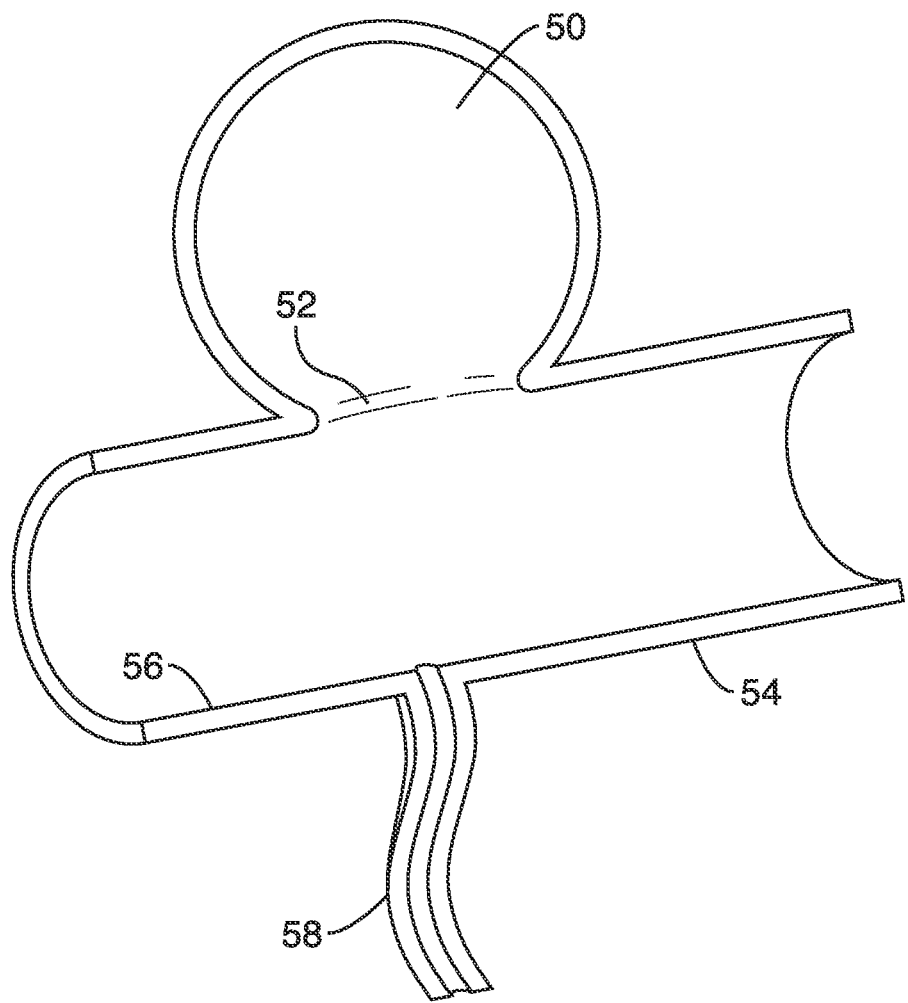
FIG. 5 is a diagram of an endovascular aneurysm.

In a preferred embodiment, the components 12, 20 of treatment stent assembly 10 are configured to be delivered through a micro catheter over a guide wire (both not shown), and deployed across the neck 52 of a target aneurysm 50 (see FIG. 5).

Outer anchoring stent 12 comprises a mesh of low-density struts 14 to allow for generally unobstructed radial flow through the struts. The struts 14 are configured to be compressed into an axially-retracted state to allow transport to the desired location within the vasculature, and then release to form an expanded state such that the OD of anchoring stent 12 contacts and engages the vasculature to be stabilized in the parent vessel, generally spanning the neck of the aneurysm. Outer anchoring stent 12 is generally very flexible due to the low density of the stent struts 14 and has a length $L_{os}$ sufficient to enable safe, stable deployment, even in a greatly curved vessel. An example of a range of length $L_{os}$ is from about 20 mm to about 45 mm. The longer the stent, the more friction that can be caused, and the density should be reduced. For an intracranial stent, an example of a range of diameter is from about 2 mm to about 5 mm.

The inner treatment stent 20 comprises a tubular mesh pattern of struts 22 that is expandable from a collapsed state to allow for axial flow through central channel 24, and is configured to rest or be housed inside of the anchoring stent 12 and preferably control the degree of blood flow into the aneurysm 50. The inner treatment stent 20 is also capable of sparing blood flow to nearby branching vessels 58 by virtue of its strut design.

Figure 2:
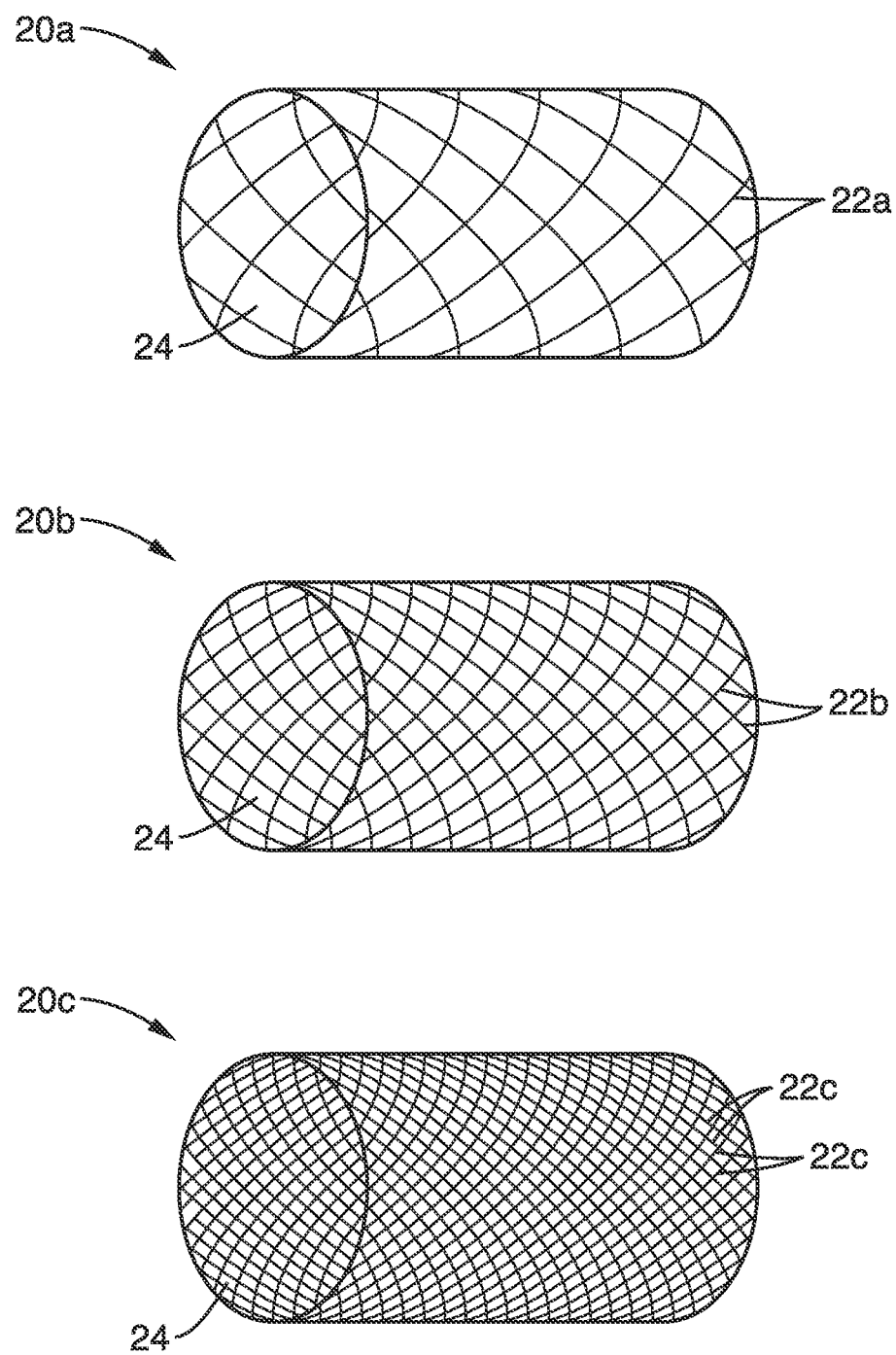
FIG. 2 shows a schematic perspective view of several variations of a symmetrical inner treatment stent configured to be used in the assembly of FIG. 1.
Figure 3:
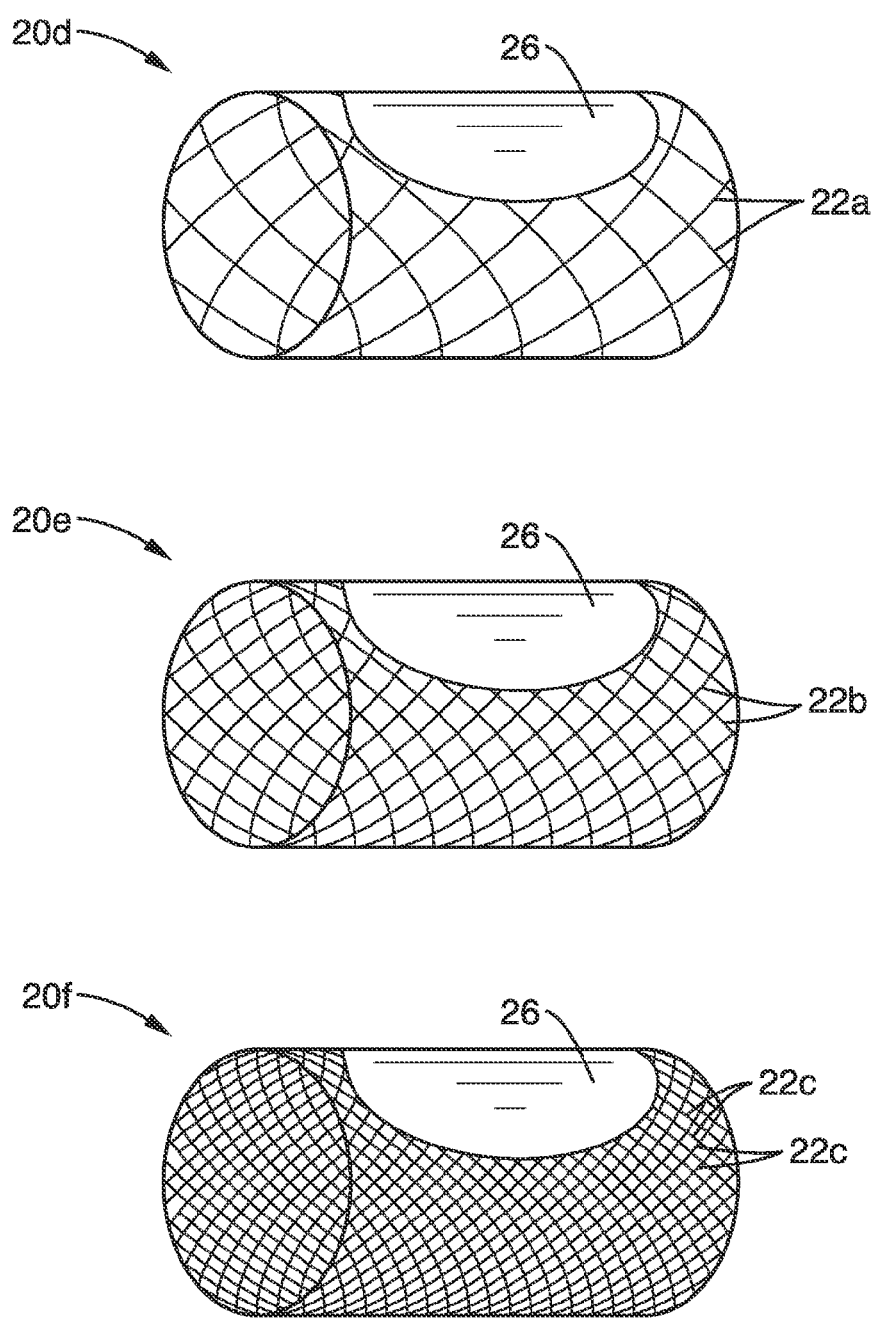
FIG. 3 shows a schematic perspective view of several variations of a symmetrical inner treatment stent with high density region configured to be used in the assembly of FIG. 1.
Figure 4:
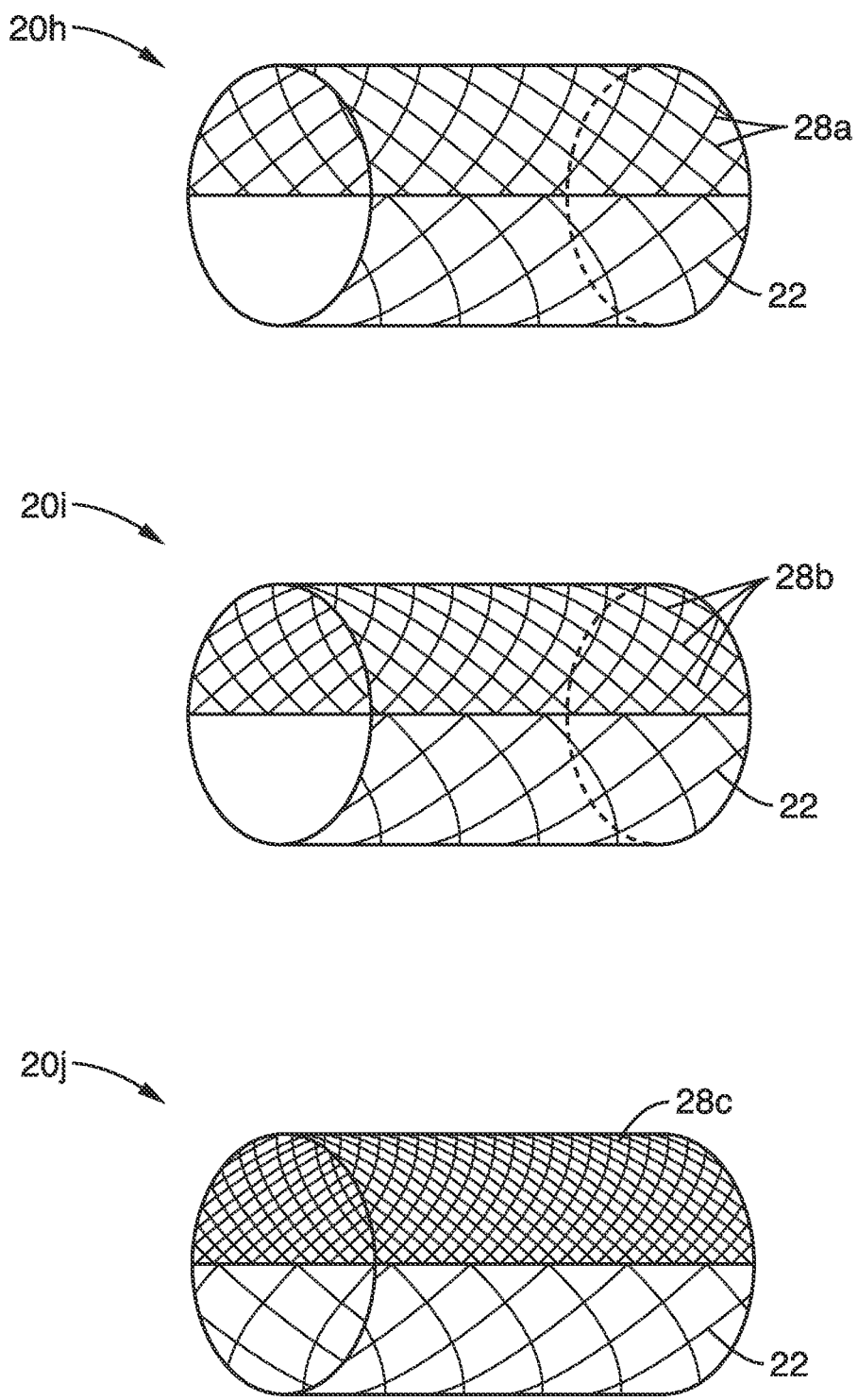
FIG. 4 shows a schematic perspective view of several variations of an asymmetrical inner treatment stent configured to be used in the assembly of FIG. 1.

Referring to FIG. 2 through FIG. 4, the inner treatment stent 20 has several important variable parameters: 1) variable density of the strut weave, 2) variable radial distribution (symmetrical and asymmetrical) of the strut weave on the stent's cylindrical surface, and 3) a 2-dimensional geographic pattern of the strut weave along the length of the cylindrical surface of the stent. The inner treatment stent 20 may also have a variable length $L_{is}$ and may be expandably deployable using mechanical, hydraulic, electrical (MEMS) or chemical means. Length $L_{is}$ is variably selected according to the size of the aneurysm neck 52, and is generally sized to span the length of aneurysm neck 52, or be slightly larger than neck 52. Length $L_{is}$ will generally be smaller than length $L_{os}$, as shown in FIG. 1. In one embodiment, the inner treatment stent 20 may be firmly seated by the antegrade blood flow within.

In a preferred embodiment, internal treatment stent 20 comprises an adjustable (i.e. variable) strut-density pattern. Thus, the stent can cover the orifice 52 of the aneurysm 50 causing blockage of blood flow (or marked reduction of blood flow) in the radial direction to occlude the aneurysm 50, while sparing blood flow to perforators or side branches 58 near the aneurysm neck (see FIG. 5).

Multiple different configurations of treatment stents 20 are contemplated, ranging from general categories of symmetrical strut treatment stents 20a through 20c (SSTS) shown in FIG. 2, SSTS treatment stents with a high strut density area 20d through 20f shown in FIG. 3, and asymmetrical strut treatment stents (ASTS) 20h through 20j shown in FIG. 4. The SSTS 20a through 20c is composed of a uniform strut density, whereas ASTS 20h through 20j may comprise strut weave densities that differ circumferentially (higher struts density and lower strut density) in the same stent, but also different, asymmetrical geometric patterns on the same 2-dimensional stent surface along its length $L_{is}$. The SSTS with high strut density area 20d through 20f is composed of homogeneous SSTS and a partial high strut density area.

Referring to FIG. 2, the density of the struts 22, which determines the porous nature of the stent wall, can be variably adjusted from low to high, with high virtually eliminating the passage of blood. For example, stent 20a may comprise a low-density (e.g., about 5% to about 10%) symmetrical pattern of struts 22a to allow for a high radial flow through the stent wall. Stent 20b may comprise a medium density (e.g., about 10% to about 20%) symmetrical pattern of struts 22b to allow for moderate radial flow through the stent wall. Stent 20c may comprise a high density (e.g., about 20% to about 30%) symmetrical pattern of struts 22c to allow for minimal to no radial flow through the stent wall. Suitable materials for the stent include, for example, various types of metals and polymers. However, with current technology, mesh density of about 35% or more can result in severe friction during deployment. It is possible to create a stent with higher density, but once you fold it and place it into the microcatheter, and deliver the stent through very tortuous vessels, it can create enormous friction. If you make the stent thinner to reduce the friction, then it looses radial force.

FIG. 3 shows SSTS 20d through 20f with high strut density area 26 that is comprised of homogeneous SSTS and a partial high strut density area 26. The density of the strut weave of SSTS 20*d* through 20*f* can be varied from low to very high, depending on the degree of blood flow obstruction desired. For example, stent 20*d* may comprise a low density symmetrical pattern of struts 22*a* to allow for high flow radially through the stent wall. Stent 20*e* may comprise a medium density symmetrical pattern of struts 22*b* to allow for moderate radial flow through the stent wall. Stent 20*e* may comprise a high density symmetrical pattern of struts 22*c* to allow for minimal to no flow radial through the stent wall. High strut density region 26 is shown as an ellipsoid area, however, varying shapes and sizes are contemplated.

FIG. 4 shows ASTS 20*h* through 20*j* with a variable, 2-dimensional geometric pattern on the surface of the cylindrical stent wall to provide additional flexibility in redirecting or obstructing blood flow. For example, inner treatment stent 20*h* comprises a first section 28*a* (upper half of cylinder) with a relatively low strut density, yet still having a higher density than the second section of struts 22 (lower half of cylinder). Inner treatment stent 20*i* comprises a first section 28*b* with a moderate strut density, and Inner treatment stent 20*j* comprises a first section 28*c* with a high strut density. While the first section 28*a* through 28*c* is shown in FIG. 4 as being a 180 degree section of the outer circumference, it is appreciated that other sizing and shapes are contemplated.

In the ASTS variations 20*h* through 20*j*, the higher strut weave density portion 28*a* through 28*c* may be positioned over/adjacent to the neck 52 of the aneurysm 50, leaving the lower density strut portion 22 on the side of perforators or branch vessels 58 to protect blood flow to them (see FIG. 5). The density of the weave 28*a* through 28*c* can be further augmented with the addition of ultra-thin Nitinol attached to the strut weave using microclips (not shown). A bioabsorbable polymer (not shown) may also be implemented and stretched over the stents 20.

FIG. 5 through FIG. 8 illustrate a method for treatment of an endovascular aneurysm 50 using the dual-rotational stent system 10 of the technology described herein. Referring to FIG. 5, the aneurism 50, vasculature 54, and adjacent branches 58 may be visualized pre-operatively (e.g. with radiographic, intravascular, or other imaging methods available in the art).

For example, a pre-procedural planning assessment may be used to generate precise 3D imaging data to produce 3D arterial models of an individual patient's cerebral aneurysm 50 and vasculature 54, which can then be used to manufacture patient-specific stent 10 configurations. In a preferred embodiment, the stent assembly 10 may be generated via a 3D printer, or stereolithography, or the like, using the 3D data set. This allows for determining prior to the procedure the best combination of anchoring stent 12 and internal treatment stent 10 that can safely occlude the neck 52 of that patient's specific cerebral aneurysm 50 anatomy, while sparing adjacent branches 58 arising from the main feeding artery.

Given the anatomical variation of perforators and side branches 58 near aneurysms 50, either a SSTS 20*a* through 20*c* or one of a wide variety of either a modified SSTS 20*d* through 20*f* with high-density region, or ASTS 20*h* through 20*j* may be selected. The SSTS 20*a* through 20*c* will be suitable when there are no perforators 58 near the target aneurysm 50, whereas the SSTS 20*d* through 20*f* with high-density region or ASTS 20*h* through 20*j* may be chosen to protect the blood flow of nearby perforators or branch vessels 58.

Figure 6:
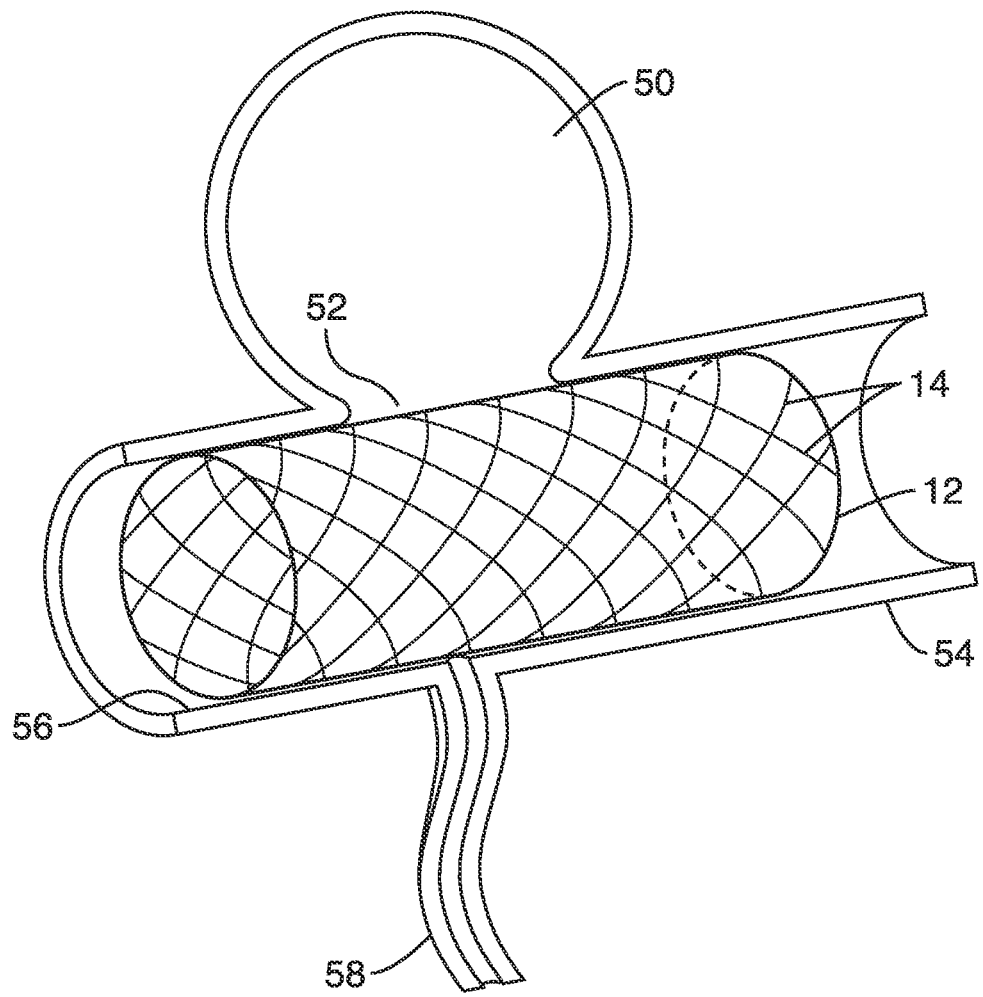
FIG. 6 is a schematic diagram of the anchoring stent of the technology described herein installed at the aneurysm site.

Referring now to FIG. 6, the anchoring stent 12 is first delivered to the treatment site in the vasculature corresponding to the aneurysm 50. The struts 14 anchoring stent 12 are configured to be compressed into an axially-retracted state to allow transport to the desired location within the vasculature 54, and then release to form an expanded state such that the OD of anchoring stent 12 contacts and engages the inside wall 56 vasculature 56 to be stabilized in the parent vessel, generally spanning the neck 52 of the aneurysm.

Figure 7:
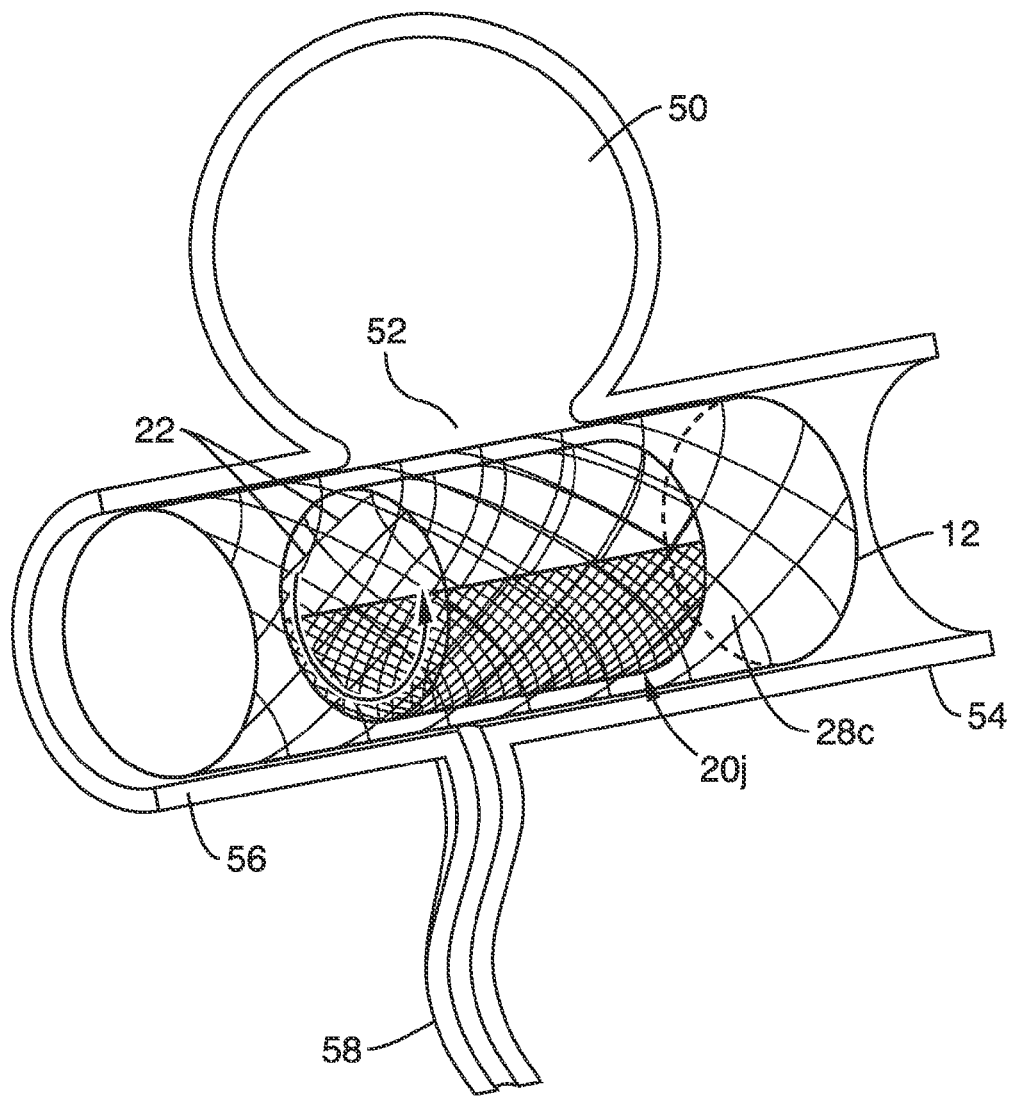
FIG. 7 is a schematic diagram of an asymmetrical inner treatment stent installed within the anchoring stent at the aneurysm site.

Referring now to FIG. 7, the treatment device 20 is then delivered into the opening 24 of the anchoring stent 12. For delivery of symmetrical treatment stents 20*a* through 20*c*, this may merely comprise insertion of the internal treatment stent 20 into the proper position within anchoring stent 12, and then securing the stent 20 in said position. For internal treatment stents 20*d* through 20*f* or 20*h* through 20*j*, radial adjustment of the internal stent 20 to the aneurysm 50 may be needed.

In FIG. 7, a high density asymmetric internal treatment stent 20*j* is shown positioned within anchoring stent 12. It is appreciated that illustration of asymmetric internal treatment stent 20*j* is for exemplary purposes only, and any internal stent configuration from 20*a* through 20*j*, or combination thereof, may be employed. As seen in FIG. 7, the internal treatment stent 20*j* is shown out of position, with low-density weave pattern 22 adjacent aneurysm neck 52.

Figure 8:
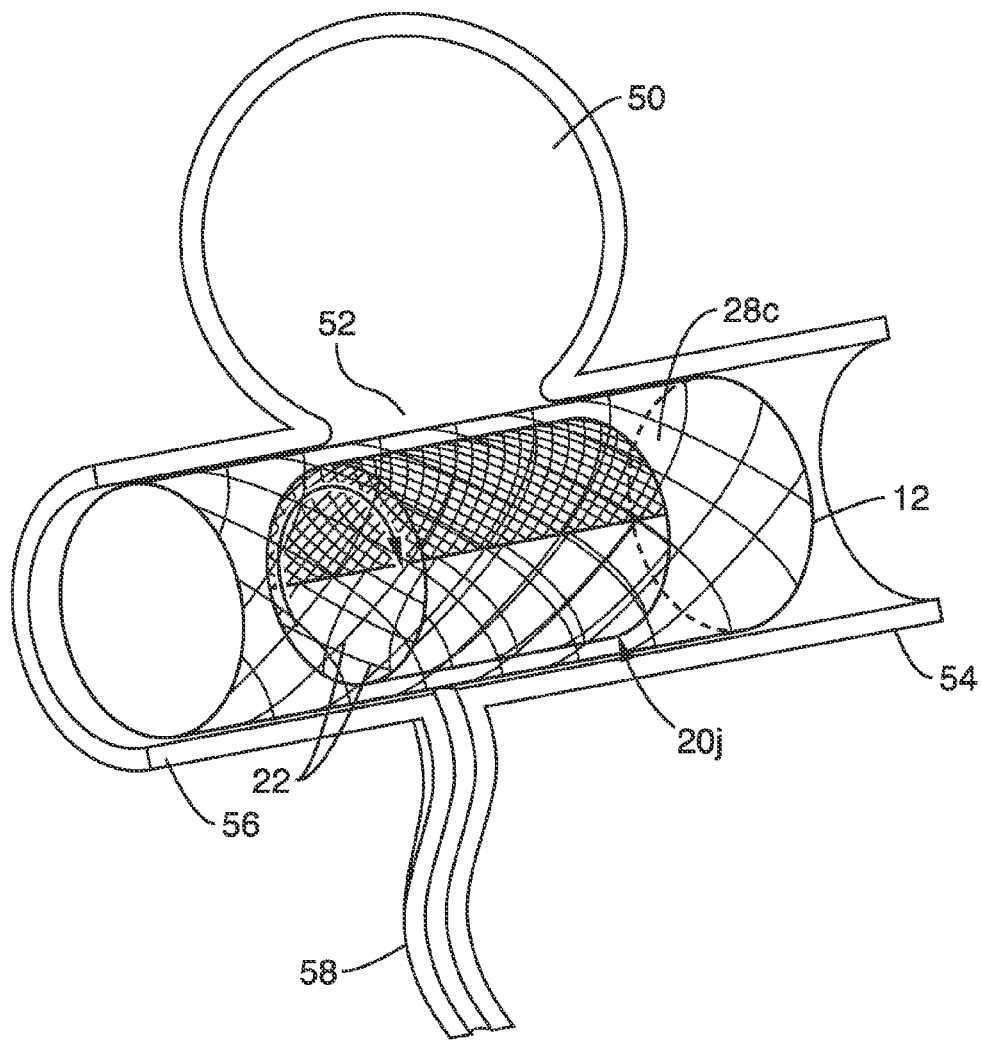
FIG. 8 is a schematic diagram of the asymmetrical inner treatment stent rotated within the anchoring stent so that the high density area asymmetrical inner treatment stent is adjacent to the aneurysm.

Referring to FIG. 8, the radial position of the strut weave 28*c* is then selected and/or adjusted (e.g. rotated about the axis of the stent 20*j*) via the delivery system according to the individual configuration/location of the cerebral aneurysm 50, such that the low-density struts 22 are positioned adjacent nearby branching vessels or perforators 58, and high-density weave 28*c* is positioned adjacent aneurysm neck 52 to minimize or cut off flow into aneurysm 50. A key feature of all the treatment stents 20*a*-20*j* is that they are rotatable inside of the anchoring stent 12, to which they are ultimately attached, in order to test the degree of blood flow change with different positions of the treatment stent 20.

In addition to the radial distribution pattern, an additional 2-dimensional geometric pattern can be added along the total or partial length $L_{is}$ of the cylindrical surface of the inner treatment stent 20 by adding one or more treatment stents. This geometric pattern will reflect the efficacy of certain patterns in either redirecting or occluding blood flow, and again, can be tailored to the specific configuration of a patient's aneurysm 50.

The length $L_{is}$ of the inner treatment stent 20 will preferably be available in different sizes (e.g. kit) so that it is specifically configured to match the neck 52 of the aneurysm 50. The length $L_{is}$ of the inner treatment stent 20 can be of relatively short length because the outer anchoring stent 12 provides stability and localization within the vessel 54. Accordingly, multiple treatment stents 20 may be positioned within the outer anchoring stent 12, if necessary, e.g. for complex aneurysms.

A family or kit of distinct stent configurations and stent sizes encompassing all of the above design variables is also contemplated In one embodiment, the pre-planning assessment may be used for placement of adjustment of "guides" (not shown) in the anchoring stent 12, such that radial rotation and manipulation during placement of the internal treatment stent 20 is minimized. The guides would allow the internal treatment occluding stent 20 to easily slide into place and also to lock into place with respect to the anchoring stent 12 once the final position has been achieved.

In another embodiment, the stent 10 combination configuration is selected via a CAD computer program (not shown) as part of pre-procedural planning. Thus, the time needed for stent selection, adjustments and manipulation of the stent system 10 to achieve the desired positioning and flow characteristics during the actual procedure is minimized, making the procedure shorter and safer. The stent system 10 of the technology described herein adds both accuracy and safety to the placement of the dual stents in treating complex cerebral aneurysms.

Given the multiplicity of complex, asymmetrical designs, the stent system 10 of the technology described herein enables minimally invasively therapy in the form of blood flow reduction and redirection without the need for conventional filling materials and associated methods.

The geometric pattern approach described above allows an extremely large number of symmetrical and asymmetrical patterns to be generated, which can be customized to alter blood flow according to a patient's personalized arterial/aneurysm anatomy. One or multiple such patterned stents 10 can be placed depending on the vascular anatomy. The hemodynamic impact of the stent 10 of the technology described herein upon the blood flow dynamics in large or giant aneurysms is nearly immediate, and allows for real time intra-procedural monitoring and intra-procedure adjustment of the stent. The stent 10 decreases intra-aneurysmal pressure, blood velocity and wall shear stress eliciting a rapid, progressive thrombosis throughout the aneurysm 50, and significantly reduces the probability of aneurysm rupture. The stent 10 provides treatment of endovascular therapy for brain aneurysms using only stent devices, without the use of coils and methods associated with them.

Accordingly, we have described a coaxial stent system in which an inner treatment stent is configured to be coaxially positioned inside an outer anchoring stent. The outer anchoring stent is adapted for insertion into a blood vessel and anchoring to the blood vessel at a position where the outer anchoring stent spans a neck of an aneurysm. We have also described a method for endovascular treatment of aneurysms.

From the discussion herein it will be appreciated that the technology described herein can be embodied in various ways, including the following:

1. An endovascular treatment apparatus, comprising: an outer anchoring stent; and an inner treatment stent; said inner treatment stent configured to be coaxially positioned inside said outer anchoring stent; said outer anchoring stent adapted for insertion into a blood vessel and anchoring to said blood vessel at a position wherein said outer anchoring stent spans a neck of an aneurysm; said inner treatment stent adapted for controlling a volume of blood flow into the aneurysm.

2. An apparatus as in any of the previous embodiments, wherein said anchoring stent comprises a plurality of flexible struts.

3. An apparatus as in any of the previous embodiments: wherein said inner treatment stent has a length; and wherein said outer anchoring stent has a length greater than the length of said inner treatment stent.

4. An apparatus as in any of the previous embodiments, wherein said treatment stent comprises a plurality of flexible struts.

5. An apparatus as in any of the previous embodiments, wherein said struts have a symmetrical weave of uniform density.

6. An apparatus as in any of the previous embodiments, wherein said struts have an asymmetrical weave of non-uniform density.

7. An apparatus as in any of the previous embodiments, wherein strut weave density is non-uniform circumferentially.

8. An apparatus as in any of the previous embodiments, wherein said weave has different geometric patterns on the same 2-dimensional surface along the length of the treatment stent.

9. An apparatus as in any of the previous embodiments, wherein the treatment stent comprises a high density region and a low-density region.

10. An apparatus as in any of the previous embodiments, wherein the treatment stent is configured to be rotated axially inside said outer anchoring stent to align at least a portion of the high-density region according to a location of the aneurysm to minimize or occlude blood flow into the aneurysm.

11. An apparatus as in any of the previous embodiments, wherein the low-density region is configured to be aligned with a perforator or branch vessel within the blood vessel to allow blood flow into the perforator or branch vessel.

12. An apparatus as in any of the previous embodiments: wherein the high density region comprises a higher strut weave density portion configured to be positioned to minimize or occlude blood flow to the aneurysm; and wherein a lower density region of the treatment stent is configured to be aligned adjacent one or more perforators or branch vessels, when the high density region is aligned adjacent the aneurysm, to allow blood flow to the one or more perforators or branch vessels.

13. A stent system for endovascular treatment of aneurysms, comprising: an outer anchoring stent; and an inner treatment stent; said inner treatment stent configured to be coaxially positioned inside said outer anchoring stent; said outer anchoring stent adapted for insertion into a blood vessel and anchoring to said blood vessel at a position wherein said outer anchoring stent spans a neck of an aneurysm; said anchoring stent comprising a plurality of flexible struts arranged in a low-density pattern to allow for radial blood flow between the struts; said inner treatment stent comprising a plurality of flexible struts configured in a pattern for controlling a volume of blood flow radially into the aneurysm.

14. A stent system as in any of the previous embodiments: wherein said inner treatment stent has a length; and wherein said outer anchoring stent has a length greater than the length of said inner treatment stent.

15. A stent system as in any of the previous embodiments, wherein said struts of the inner treatment stent have a symmetrical weave of uniform density.

16. A stent system as in any of the previous embodiments, wherein said struts of the inner treatment stent have an asymmetrical weave of non-uniform density.

17. A stent system as in any of the previous embodiments, wherein strut weave density is non-uniform circumferentially.

18. A stent system as in any of the previous embodiments, wherein said weave has different geometric patterns on the same 2-dimensional surface along the length of the treatment stent.

19. A stent system as in any of the previous embodiments, wherein the treatment stent comprises a high density region and a low-density region.

20. A stent system as in any of the previous embodiments, wherein the treatment stent is configured to be rotated axially inside said outer anchoring stent to align at least a portion of the high-density region according to a location of the aneurysm to minimize or occlude blood flow into the aneurysm.

21. A stent system as in any of the previous embodiments, wherein the low-density region is configured to be aligned with a perforator or branch vessel within the blood vessel to allow blood flow into the perforator or branch vessel.

22. A stent system as in any of the previous embodiments: wherein the high density region comprises a higher strut weave density portion configured to be positioned to minimize or occlude blood flow to the aneurysm; and wherein a lower density region of the treatment stent is configured to be aligned adjacent one or more perforators or branch vessels, when the high density region is aligned adjacent the aneurysm, to allow blood flow to the one or more perforators or branch vessels.

23. A method for endovascular treatment of a target aneurysm within a blood vessel, comprising: delivering an outer anchoring stent into the blood vessel and anchoring the outer anchoring stent to said blood vessel at a position wherein said outer anchoring stent spans a neck of the target aneurysm; said anchoring stent comprising a plurality of flexible struts arranged in a low-density pattern to allow for radial blood flow between the struts; and coaxially positioning an inner treatment stent inside said outer anchoring stent; wherein the inner treatment stent comprises a plurality of flexible struts configured in a pattern for controlling a volume of blood flow radially into the aneurysm.

24. A method as in any of the previous embodiments: wherein said inner treatment stent has a length; and wherein said outer anchoring stent has a length greater than the length of said inner treatment stent.

25. A method as in any of the previous embodiments, wherein said struts of the inner treatment stent have a symmetrical weave of uniform density.

26. A method as in any of the previous embodiments, wherein said struts of the inner treatment stent have an asymmetrical weave of non-uniform density.

27. A method as recited in any of the previous embodiments, wherein strut weave density is non-uniform circumferentially.

28. A method as in any of the previous embodiments, wherein said weave has different geometric patterns on the same 2-dimensional surface along the length of the treatment stent.

29. A method as in any of the previous embodiments, wherein the treatment stent comprises a high density region and a low-density region.

30. A method as in any of the previous embodiments, further comprising: axially rotating the treatment stent inside said outer anchoring stent to align at least a portion of the high-density region according to a location of the aneurysm to minimize or occlude blood flow into the aneurysm.

31. A method as in any of the previous embodiments, further comprising: aligning the low-density region with a perforator or branch vessel within the blood vessel to allow blood flow into the perforator or branch vessel.

32. A method as in any of the previous embodiments, wherein the high density region comprises a higher strut weave density portion, the method further comprising: positioning the high-density portion adjacent the aneurysm to minimize or occlude blood flow to the aneurysm; and aligning the lower density region of the treatment stent to be adjacent one or more perforators or branch vessels to allow blood flow to the one or more perforators or branch vessels.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An endovascular treatment apparatus, comprising:
an outer anchoring stent; and
an inner treatment stent;
said inner treatment stent configured to be coaxially positioned inside said outer anchoring stent;
said outer anchoring stent adapted for insertion into a blood vessel and anchoring to said blood vessel at a position wherein said outer anchoring stent spans a neck of an aneurysm;
said inner treatment stent comprising a plurality of struts disposed in a configuration for controlling a volume of blood flow into the aneurysm;
wherein said struts have a circumferentially asymmetrical weave of non-uniform density;
wherein the inner treatment stent is free to rotate with respect to the outer anchoring stent so as to locate the asymmetrical weave of the inner treatment stent circumferentially adjacent to the aneurysm.

2. An apparatus as recited in claim 1, wherein said anchoring stent comprises a plurality of flexible struts.

3. An apparatus as recited in claim 1:
wherein said inner treatment stent has a length; and
wherein said outer anchoring stent has a length greater than the length of said inner treatment stent.

4. An apparatus as recited in claim 1, wherein said treatment stent comprises a plurality of flexible struts.

5. An apparatus as recited in claim 2, wherein said flexible struts have a symmetrical weave of uniform density.

6. An apparatus as recited in claim 1, wherein said weave has different geometric patterns on the same 2-dimensional surface along the length of the treatment stent.

7. An apparatus as recited in claim 1, wherein the treatment stent comprises a high density region and a low-density region.

8. An apparatus as recited in claim 7, wherein the treatment stent is sized to allow the treatment stent to be rotated axially inside said outer anchoring stent to align at least a portion of the high-density region adjacent a location of the aneurysm to minimize or occlude blood flow into the aneurysm.

9. An apparatus as recited in claim 8, wherein the low-density region is configured to be aligned with a perforator or branch vessel within the blood vessel to allow blood flow into the perforator or branch vessel.

10. An apparatus as recited in claim 7:
wherein the high density region comprises a higher strut weave density portion configured to be positioned to minimize or occlude blood flow to the aneurysm; and
wherein a lower density region of the treatment stent is configured to be aligned adjacent one or more perforators or branch vessels, when the high density region is aligned adjacent the aneurysm, to allow blood flow to the one or more perforators or branch vessels.

11. A stent system for endovascular treatment of aneurysms, comprising:
an outer anchoring stent; and
an inner treatment stent;
said inner treatment stent configured to be coaxially positioned inside said outer anchoring stent;
said outer anchoring stent adapted for insertion into a blood vessel and anchoring to said blood vessel at a position wherein said outer anchoring stent spans a neck of an aneurysm;
said anchoring stent comprising a plurality of flexible struts arranged in a low-density pattern to allow for radial blood flow between the struts;
said inner treatment stent comprising a plurality of flexible struts disposed in a pattern for controlling a volume of blood flow radially into the aneurysm;
wherein said inner treatment struts have a circumferentially asymmetrical weave of non-uniform density;
wherein the inner treatment stent is free to rotate with respect to the outer anchoring stent so as to locate the asymmetrical weave of the inner treatment stent circumferentially adjacent to the aneurysm.

12. A system as recited in claim 11:
wherein said inner treatment stent has a length; and
wherein said outer anchoring stent has a length greater than the length of said inner treatment stent.

13. A system as recited in claim 11, wherein said struts of the outer anchoring stent have a symmetrical weave of uniform density.

14. A system as recited in claim 11, wherein said weave has different geometric patterns on the same 2-dimensional surface along the length of the treatment stent.

15. A system as recited in claim 11, wherein the treatment stent comprises a high density region and a low-density region.

16. A system as recited in claim 15, wherein the treatment stent is configured to be rotated axially inside said outer anchoring stent to align at least a portion of the high-density region according to a location of the aneurysm to minimize or occlude blood flow into the aneurysm.

17. A system as recited in claim 16, wherein the low-density region is configured to be aligned with a perforator or branch vessel within the blood vessel to allow blood flow into the perforator or branch vessel.

18. A system as recited in claim 15:
wherein the high density region comprises a higher strut weave density portion configured to be positioned to minimize or occlude blood flow to the aneurysm; and
wherein a lower density region of the treatment stent is configured to be aligned adjacent one or more perforators or branch vessels, when the high density region is aligned adjacent the aneurysm, to allow blood flow to the one or more perforators or branch vessels.

* * * * *